United States Patent [19]

Ohnishi et al.

[11] Patent Number: 4,540,569

[45] Date of Patent: Sep. 10, 1985

[54] METHOD FOR TREATMENT OF ALLERGIC DISORDERS AND IMMUNE COMPLEX DISEASES

[75] Inventors: Haruo Ohnishi, Funabashi; Hiroshi Kosuzume, Yokohama; Yasuo Suzuki, Kawaguchi; Ei Mochida, Toshima, all of Japan

[73] Assignee: Mochida Seiyaku Kabushiki Kaisha, Tokyo, Japan

[21] Appl. No.: 365,465

[22] Filed: Apr. 5, 1982

Related U.S. Application Data

[63] Continuation-in-part of Ser. No. 345,152, Feb. 2, 1982, abandoned.

[30] Foreign Application Priority Data

Feb. 10, 1981 [JP] Japan .................................. 56-18429
Jun. 4, 1981 [JP] Japan .................................. 56-86147
Jul. 18, 1981 [JP] Japan .................................. 56-112856

[51] Int. Cl.$^3$ ............................................ A61K 37/48
[52] U.S. Cl. ..................................................... 424/94
[58] Field of Search ........................................... 424/94

[56] References Cited

PUBLICATIONS

Seikagaku—Chem. Abst., vol. 96 (1982).
Chem. Abstracts—Chemical Substance Index—10th Collect. (1977–1981), p. 37485cs.
Mirsky et al., Source, Properties and Assays of Uropepsin, "Uropepsin Excretion by Man", pp. 818–839.

*Primary Examiner*—Sam Rosen
*Attorney, Agent, or Firm*—Parkhurst & Oliff

[57] ABSTRACT

Therapeutic agent for the treatment of allergic disorders, immune complex diseases and tumors, which contains a human urinary acid protease as an active ingredient, and a method for treating allergic disorders, immune complex diseases and tumors by administering the said acid protease, which has never been used as a therapeutic agent for allergic disorders, immune complex diseases and tumors. Since the acid protease is a protein of human origin, the probability of adverse reactions such as anaphylactic shock due to the antigenicity of the acid protease is believed to be extremely small.

22 Claims, 4 Drawing Figures

METHOD FOR TREATMENT OF ALLERGIC DISORDERS AND IMMUNE COMPLEX DISEASES

This is a continuation-in-part application of U.S. patent application Ser. No. 345,152 filed Feb. 2, 1982 entitled: "Therapeutic agent and method for treatment of allergic disorders, immune complex diseases and tumors", now abandoned.

BACKGROUND OF THE INVENTION

Allergic disorders are induced by antigen-antibody reactions. When an individual has been immunologically primed or sensitized, further contact with antigen can lead not only to secondary boosting of the immune response but can also cause tissue-damaging reactions, i.e., allergic disorders. The mechanism of pathogenesis of allergic disorders is presently believed as follows:

An individual produces antibodies after exposure to pathogenic antigen. Secondary antigen exposure causes antigen-antibody reaction and the formed antigen-antibody complexes deposit on the tissues, and chemical mediators are released from sensitized cells. Then these mediators and/or the deposited antigen-antibody complexes damage tissues.

Pathogenic antigens are xenogenic antigens (inhaled allergen, food allergen, drugs and so on), allogenic antigens and autologus antigens which are denatured autologus components of tissues or organs, and act as foreign substances.

So-called allergic disorders may be classified into four types;

(1) Type I allergy (anaphylactic-type), in which the antigen reacts with a specific class of antibody bound to mast cells or circulating basophils through a specialized region of the antibody. This leads to degranulation of the cells and release of vasoactive mediators;

(2) Type II allergy (cytotoxic-type), in which the antibodies on the cell surface bind to an antigen and cause several reactions such as opsonic or immune phagocytosis of the cell, and cell lysis by the action of the complement system;

(3) Type III allergy (Arthus type; immune complex mediated), in which a complex is formed between antigen and humoral antibody and causes activation of the complement system, platelet aggregation, microthrombi formation, and so on;

(4) Type IV allergy (cell-mediated or delayed-type), in which thymus-derived lymphocytes (T cells) with specific receptors are stimulated by antigens and release mediators. In case of tissue rejection, these lymphocytes transform to kill certain cells with the histocompatibility antigen of the graft.

Among the allergic reactions, Types I, III and IV allergies participate in, for example, bronchial asthma and each of these reactions is considered independently, or in combination to cause these disorders. The mechanism of induction of allergic disorders is considered as follows: an antigen which enters an organism is treated by macrophages and the immunological information is transmitted to the T cell-B cell system. The B cells which have received the information produce anibody (IgE antibody is mainly produced in Type I allergy and IgG antibody in Type II or Type III allergy). IgE antibody binds to basophils in circulation or to mast cells in the tissues, thereby establishing the sensitized state. Hereafter, the same antigen which enters the sensitized organism binds with the antibody on these cells and releases chemical mediators, such as histamine, or slow reacting substances of anaphylaxis (SRS-A). The chemical mediators thus released induce allergic symptoms such as erythema, edema, or increase of glandular secretion caused by contraction of smooth muscles and increase of capillary permeability. On the other hand, IgG-antibody binds polymorpho-nuclear leukocytes to achieve sensitization, and SRS-A as a chemical mediator is thought to be secreted.

Agents for treatment of allergic disorders can achieve their therapeutic purpose by inhibiting any step in the above-mentioned processes. For example, xanthine derivatives, $\beta$-adrenergic stimulants ($\beta$-stimulants) or corticosteroids are used for treatment of bronchial asthma. However, unfavorable adverse reactions have often been observed in these drugs. For example, palpitation and tachycardia are reported in patients receiving xanthine derivatives and $\beta$-stimulants. Furthermore, corticosteroids cause adverse reactions such as peptic ulcer and complication of bacterial infection. Anti-histamine agents are not effective for bronchial asthma; these agents sometimes make the asthma even worse by making it difficult to expectorate tracheal secretions.

Immune complex diseases, represented by rheumatoid arthritis, systemic lupus erythematosus (SLE) and lupus nephritis, as implied by the name, are diseases which are induced by complexes of antigens with antibodies, i.e., immune complexes, and are type III allergies. Although the mechanism of occurence of these diseases is complicated and has many points which are left unclear, it is generally believed to follow the course described below.

When bacterial or viral infections damage tissues, antibodies are produced against newly formed autoantigens or virally infected cells to form immune complexes. Since these immune complexes activate the complement system and platelets, vasoactive substances such as histamine and serotonin are released and the permeability of the blood vessels is increased. Then, the immune complexes in circulation enter and deposit along the basement membrane of the vessel wall whose permeability has been increased. Where the immune complexes have deposited, polymorphonuclear leukocytes are gathered by the action of the leukocyte chemotactic factors which have been formed by the action of the complement to the deposited immune complexes. The polymorphonuclear leukocytes, reacting with the immune complexes, release various tissue-damaging substances such as cathepsins D and E, collagenase, elastase and permeability factors, and these substances eventually damage the tissue. In patients with immune complex diseases such as SLE, levels of the complement in the serum are generally low and aggravation of the disease conditions is closely correlated with the decrease of the complement levels. This decline is thought to be due to plentiful consumption of the complement at the site of the reaction between antigens and antibodies taking place such as in kidneys and blood vessels. Further, the immune complexes also are related to blood coagulation systems, and it is believed that the immune complexes cause serious symptoms through diverse mechanism for example by acceleration of fibrinoid deposition on the damaged tissues.

Today, there are several kinds of agents for the treatment of immune complex diseases: immunosuppressive agents such as steroids which suppress activation of the immune system, anti-inflammatory agents which reduce local inflammations and pain, or anticoagulative agents and antiplatelet agents which serve to improve abnormalities of the coagulation-fibrinolysis system in the blood vessels. However, these agents are not satisfactorily effective and are associated with strong adverse reactions. Thus, development of a medicine which is safe and highly effective in the treatment of the diseases is strongly desired.

Furthermore, many agents have been developed for the treatment of malignant tumors.

The anti-tumor agents are classified roughly into two types. The first includes so called cytotoxic drugs which directly suppress the growth of tumors. The second includes the drugs which indirectly control the growth of tumors by activating the immunological protective functions of the host. However, the former do not exhibit sufficient selective cytotoxicity against the tumor cells and are toxic also against normal cells, whereby the total amount of the agent which can be used is considerably limited. On the other hand, the latter, i.e., immunopotentiators, are generally safely used, less frequently exhibiting unfavorable adverse reactions compared to the former. However, tumors are originated from the normal cells of the patient, so that the tumor may not sufficiently be recognized as a foreign substance. Therefore, some immunopotentiators have an essential problem that they do not elicit sufficient anti-tumor effect.

SUMMARY OF THE INVENTION

An object of this invention is to provide an agent for the treatment of allergic disorders, immune complex diseases and tumors, which contains as an active ingredient a human urinary acid protease.

More specifically, the object of this invention is to provide a therapeutic agent for allergic disorders, immune complex diseases and tumors causing no adverse reactions.

Another object of this invention is to provide a method for treating allergic disorders, immune complex diseases and tumors by using a human urinary acid protease.

DETAILED DESCRIPTION OF THE INVENTION

Figure 1:
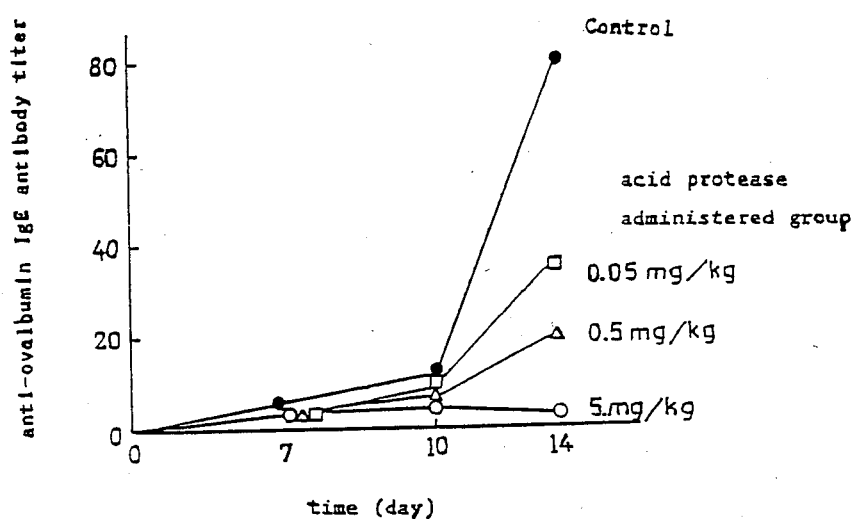
FIG. 1 shows the results of Experiment 1.

Under the background mentioned above, the present inventors have intensively investigated for the purpose of developing an effective therapeutic agent for treatment of allergic disorders, immune complex diseases and tumors. As the result, the inventors have found the facts that a human urinary acid protease exhibits a strong anti-allergic effect, remarkably suppresses various immune complex diseases, and also shows an excellent anti-tumor effect. The present invention has been accomplished based upon the above findings.

The acid protease which constitutes the active ingredient of the agents of this invention is a known enzyme (Mirsky et al: J. Clin. Invest. 27, 818, 1948) which has never been used as a therapeutic agent for allergic disorders, immune complex diseases and tumors. The acid protease can be obtained from human urine by suitably combining ordinary methods for isolating proteins such as salting out, adsorption chromatography on inorganic adsorbents, ion-exchange chromatography on an ion-exchange resin or gel chromatography using a molecular sieve.

As a non-limiting example, human urine is passed through a DEAE-cellulose column equilibrated with 0.1 M acetate buffer solution (pH 5.3) by the method of Seijffers et al. (American Journal of Physiology, 206, 1106, 1964) so as to have the acid protease adsorbed on the column. The protease is then eluted with the same buffer solution containing 0.3M sodium chloride. The eluate is concentrated, then further purified by gel chromatography using Sephadex G-100, and subjected to an acid treatment. Thus may be obtained the acid protease of this invention. The term "human urinary acid protease" is intended in this specification to mean the acid protease which may have the following physical and chemical properties and may be obtained from human urine.

The acid protease obtained by the above method is found to possess a molecular weight of 32,000–38,000 by gel chromatography on Sephadex G-100. It has an isoelectric point in the range of pH 1 to 3 by isoelectric-focusing on Ampholine. It has a maximum absorption at 278 nm, shows a positive reaction to ninhydrin and is readily soluble in water and insoluble in ether and chloroform. The acid protease shows an excellent hydrolytic activity in an acidic range, pH value less than 7, when hemoglobin is used as a substrate. The acid protease is inhibited by pepstatin. The activity of the acid protease remains stable in an acidic range, pH value less than 7, while the acid protease loses its activity in alkaline range, pH value over 8.

The following is an example of the procedure for isolation and purification of the acid protease in the present invention. However, as a matter of course, this example is merely illustrative of the procedure of isolation and purification of the acid protease and not intended to limit the method thereof.

Example of the procedure for the isolation and purification:

One hundred liter of human urine was concentrated to about one-thousandth of its initial volume using pressure ultrafiltration instrument (Pellicon ®, Millipore Co., and Diaflo ®, Amicon Co.) with a cut off of 10,000 daltons. One hundred mililiter of the concentrated urine was applied to a DEAE-cellulose (Whatman co.) column (2.5×20 cm ) equilibrated with 0.1M acetate buffer (pH 6.0) and eluted with the same buffer containing 0.3M sodium chloride. The eluate was concentrated about to 100 ml by ultrafiltration and subjected to dialysis. The dialyzed solution was then applied to a DEAE-Sepharose (Pharmacia Co.) column (2.5×20 cm ) under the same condition described above. The eluted fraction was concentrated to about 10 ml, and applied to a Sephadex G-100 gel filtration column (2.5×90 cm) for further purification and simultaneous removal of pyrogens. About 80 ml of the solution thus obtained was adjusted to pH 2 with hydrochloric acid, followed by 10-minute incubation at 37° C. Then the solution was lyophilized to give about 20 mg of the acid protease.

Now, the pharmacological action and toxicity of this acid protease will be described with reference to typical experiments below. The human urinary acid protease in this specification is not necessarily isolated and purified completely, and it can be used in the crude state so long as the impurities do not interrupt the pharmacological activities of the acid protease.

EXPERIMENT 1

Suppressive effect on production of anti-ovalbumin IgE antibody

A group of 10 Wistar male rats weighing 180–200 g was used. 0.1 mg of ovalbumin and 20 mg of aluminum hydroxide gel were injected intraperitoneally. Starting from the next day, acid protease was injected intravenously once a day for 14 days. The sera were collected 7, 10 and 14 days after the injection of ovalbumin and the anti-ovalbumin IgE antibody in the serum was determined by the homologus PCA reaction of the rats (H. Maruyama, et al., Folia Pharmacologica Japonica, 74, 179, 1978). The results are shown in FIG. 1.

Production of anti-ovalbumin IgE antibody was significantly suppressed.

EXPERIMENT 2

Suppressive Effect on Bronchial Asthma

A group of 10 Wistar male rats weighing 180–200 g was used. 0.1 mg of ovalbumin and 20 mg of aluminum hydroxide gel were injected intraperitoneally. Starting from the next day, acid protease was injected intravenously once a day for 14 days. On the 14th day 25 mg/kg of ovalbumin was injected intravenously to induce bronchial asthma. The tracheal contraction thus induced was measured by the method of Konzett and Rossler (Arch. Exptl. Path. Pharmacol. 195, 71, 1940). The contraction rate of the trachea was calculated regarding contraction of control group as 100. The results are shown in Table 1.

TABLE 1

|  |  | contraction rate of trachea (%) |
|---|---|---|
| Control |  | 100 |
| Acid protease | 0.05 mg/kg | 72 |
|  | 0.5 mg/kg | 47 |
|  | 5 mg/kg | 24 |

The tracheal contraction was significantly suppressed by adminstration of the acid protease.

EXPERIMENT 3

Hydrolysis of Immune Complex

Fifteen mg of a soluble immune complex [human IgG-rabbit anti-human IgG antibody] and 3 mg of the acid protease, trypsin, α-chymotrypsin or plasmin were dissolved in 1 ml of phosphate buffer solution (0.06M, pH 6.0) and incubated at 37° C. for 60 minutes. The reaction was stopped by the addition of 1 ml of 20% aqueous solution of perchloric acid. The supernatant was measured for absorbance at 280 nm to calculate the rate of the hydrolysis. The same procedure was repeated using human IgG instead of the immune complex. The ratio of the obtained hydrolysis rate of immune complex to that of human IgG was calculated. The results are shown in Table 2.

Compared with the other proteases, the acid protease hydrolyzed the soluble immune complex more selectively than the normal human IgG.

TABLE 2

|  | Relative rate of hydrolysis | | Hydrolysis ratio (immune complex/ human IgG) |
|---|---|---|---|
|  | Human IgG | Immune complex |  |
| Acid protease | 100 | 380 | 3.8 |
| Trypsin | 130 | 169 | 1.3 |
| α-Chymotrypsin | 22 | 26 | 1.2 |
| Plasmin | 26 | 29 | 1.1 |

EXPERIMENT 4

Hydrolysis of Immune Complex

Fifteen mg of a soluble immune complex [human IgG-rabbit anti-human IgG antibody] and 0.3 mg of the acid protease or trypsin were dissolved in 1 ml of phosphate buffer solution (0.06M, pH 6.0) and 250 μl of either rat serum or the same phosphate buffer solution was added to the mixture. Then the mixture was incubated at 37° C. for 60 minutes. After completion of the reaction, the remaining human IgG was measured by the single radial immunodiffusion method using rabbit anti-human IgG serum so as to determine the ratio of the hydrolyzed immune complex to the initially incubated immune complex. The results are shown in Table 3.

It was found that the hydrolytic activity of the acid protease on immune complex was not affected by the addition of serum. In contrast, the hydrolytic activity of trypsin was markedly reduced by the addition of serum.

TABLE 3

|  | Ratio of hydrolysis (%) | |
|---|---|---|
|  | absence of serum | Presence of serum |
| Acid protease | 35 | 35 |
| Trypsin | 19 | 2 |

EXPERIMENT 5

Suppressive Effect on Thyroiditis

Suppressive effect of the acid protease on thyroiditis was investigated according to the method of Kotani et al. (Clinical Immunology, 9, 635, 1977). A group of 10 BFU/HDK male rats (six weeks of age) was subjected to thymectomy and exposed to four repeated X-ray irradiations each of 200 rads every two weeks. After 14 weeks following the thymectomy, these rats were sacrificed. The thyroid gland of each rat was removed and embedded in a paraffin block, then stained with hematoxylin-eosin or with azan, and examined for the degree of the infiltration of mononuclear cells, destruction of endoplasmic reticulum and glandular fibrosis so as to estimate the severity of the thyroiditis according to the grades of 0 to 4. The acid protease was administered intravenously once a day. As a control, the acid protease was inactivated and administered. The results are shown in Table 4.

Compared to the control, it was found that the acid protease decreased both occurrence and severity of thyroiditis in a dose dependent manner.

TABLE 4

|  | Occurrence (%) | Severity |
|---|---|---|
| Control | 90 | 3.4 ± 0.3 |
| Acid protease |  |  |
| 1 mg/kg | 80 | 2.8 ± 0.4 |

TABLE 4-continued

|  | Occurrence (%) | Severity |
|---|---|---|
| 3 mg/kg | 60 | 2.0 ± 0.1* |
| 10 mg/kg | 40* | 1.3 ± 0.1** |

*p < 0.05,
**p < 0.01

EXPERIMENT 6

Suppressive Effect on Immune Complex Nephritis

To a group of 10 C57BL male mice, 200 mg/kg of human IgG-rabbit anti-human IgG antibody complex was injected intravenously three times a day at an interval of 8 hours for three days. On the fourth day, the animals were sacrificed and the kidneys were removed. Deposition of the immune complex in the glomeruli was observed by the fluorescent antibody technique using goat anti-rabbit IgG antibody, labeled with fluorescein isothiocyanate. Further, the immune complex content in the serum was measured by the Clq binding assay. Urinary protein was measured with commercial test paper for the 34 mice from which urine had been collected before sacrifice. The acid protease was administered intravenously three times daily starting immediately after the injection of the immune complex. As a control, inactivated acid protease was given. The results are shown in Table 5.

The immune complex content in the serum was decreased and the incidence of proteinuria and deposited immune complex in glomeruli were decreased by the administration of the acid protease.

TABLE 5

|  | Immune complex content in serum (μg/ml) | Proteinuria (Number of positive mice[a]/total number of mice tested) | Deposition of Immune complex on glomerulus (Number of positive mice/total number of mice used) |
|---|---|---|---|
| Control | 156 ± 18 | 7/8 | 10/10 |
| Acid protease |  |  |  |
| 0.3 mg/kg | 128 ± 9 | 5/7 | 8/10 |
| 1.0 mg/kg | 88 ± 12* | 4/10 | 5/10* |
| 3.0 mg/kg | 53 ± 7** | 3/9* | 2/10** |

[a]Mice showing proteinuria grade 3 or 4
*p < 0.05,
**p < 0.01

EXPERIMENT 7

Suppressive Effect on Masugi Nephritis

Figure 2:
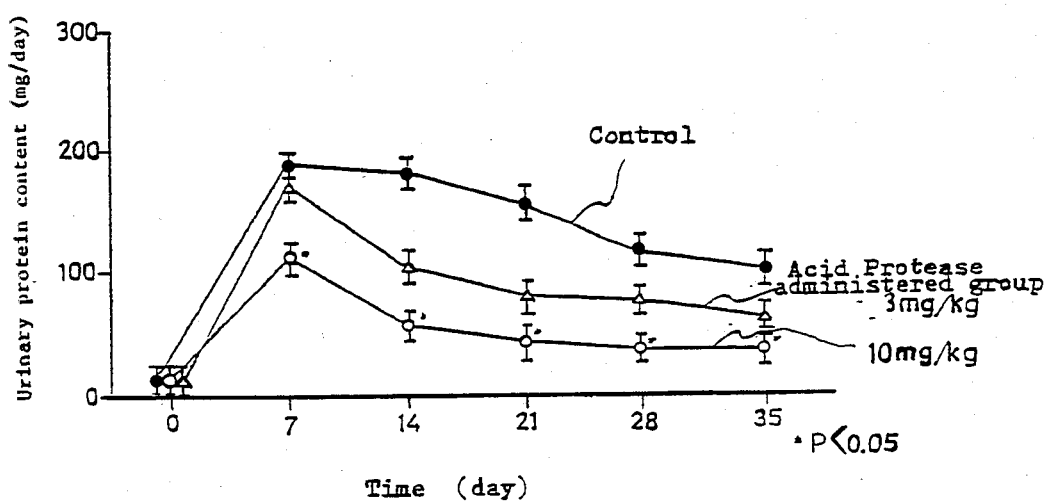
FIG. 2 and FIG. 3 show the results of Experiment 7.
Figure 3:
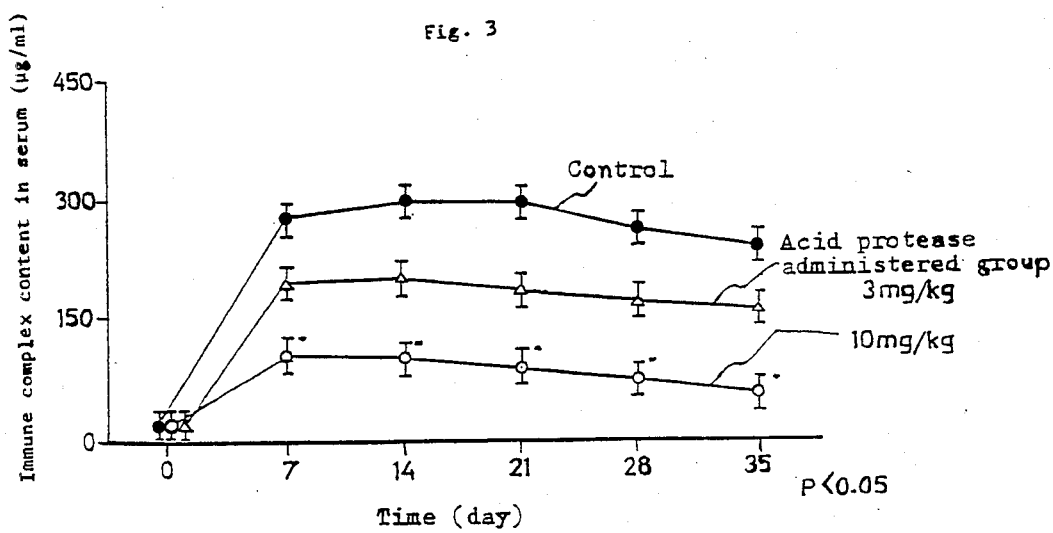

By the method of Suzuki et al. (Folia Pharmacologica Japonica, 68, 572, 1972), rabbit anti-rat kidney serum was administered intravenously to a group of 10 Wistar male rats at a dose of 5 ml/kg. The acid protease was administered intravenously once a day after the administration of the anti-kidney serum. The immune complex content in the serum and protein content in the urine were measured weekly. As a control, inactivated acid protease was given. The results are shown in FIG. 2 and FIG. 3.

In the group treated with the acid protease, a decrease in the protein content in urine and decrease in the immune complex content in serum were observed.

EXPERIMENT 8

Suppressive Effect on Spontaneous Lupus Nephritis in Mice

The method of Abe et al. (The Ryumachi, 14, 43, 1974) was used.

Figure 4:
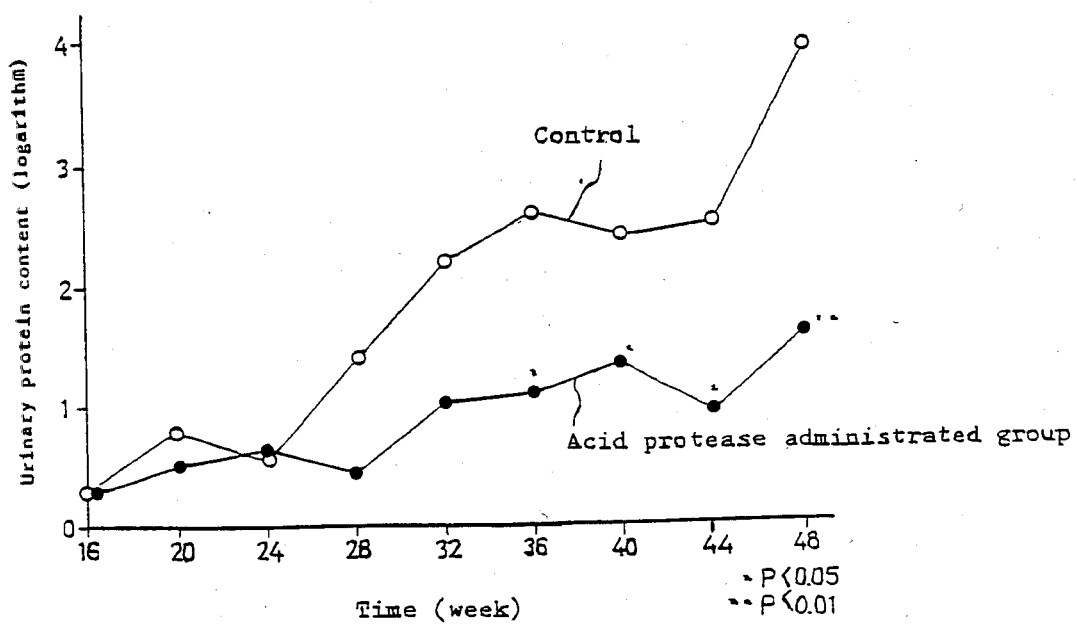
FIG. 4 shows the results of measurement of urinary protein content in Experiment 8. The urinary protein content was graded from 0 to 4 by the degree of coloration of commercially available protein test paper, and the average protein content for each group was calculated.

To a group of 16 16-week old female mice $(NZB \times NZW)F_1$, the acid protease was injected intravenously at a dose of 10 mg/kg once a day. As a control, inactivated acid protease was given. At intervals of 4 weeks, the protein content in the urine was tested with commercial test paper for grades from 0 to 4. The results are shown in FIG. 4.

Six mice from each group were sacrificed at the age of 32 weeks for the observation of cell infiltration into the renal glomeruli.

The administration of the acid protease was continued in the remaining mice from each group to determine the survival rate at the age of 50 weeks. The results are shown in Table 6.

By the administration of the acid protease, increase in the urinary protein was significantly suppressed, the cell infiltration was decreased and the survival rate was increased. These results indicate that the acid protease suppresses the lupus nephritis in mice.

TABLE 6

|  | Control group | Group treated with the acid protease |
|---|---|---|
| Cell infiltration | Heavy infiltration of small lymphocyte and plasma cell | Slight infiltration around the vessel wall |
| Survival rate | 20% | 80%* |

*p < 0.05

EXPERIMENT 9

Suppressive Effect on Chronic Active Hepatitis

In accordance with the method of Mayer et al. (British Journal of Experimental Pathology, 55, 498, 1974), human liver LSP (liver specific membrane lipoprotein) was repetitively injected together with Freund's complete adjuvant to a group of 10 rabbits to induce chronic active hepatitis. The acid protease was administered intravenously to the rabbits once a day for two weeks. Two weeks after the induction of the hepatitis, serum GOT and GPT activities were measured. As a control, inactivated acid protease was given. The results are shown in Table 7.

The acid protease suppressed the increase of serum GOT, GPT activities in a dose-dependent manner.

TABLE 7

|  | GOT activity (unit/ml) | GPT activity (unit/ml) |
|---|---|---|
| Control | 337.5 ± 34.5 | 395.1 ± 40.5 |
| Acid protease |  |  |
| 1 mg/kg | 311.5 ± 27.4 | 351.2 ± 37.8 |
| 3 mg/kg | 256.2 ± 41.1 | 301.5 ± 29.7 |
| 10 mg/kg | 193.3 ± 36.3** | 245.7 ± 31.4** |

**p < 0.01

EXPERIMENT 10

Suppressive Effect on Arthritis

By the method of Tsukada et al. (The Ryumachi, 16, 255, 1976), 4 ml of a soluble bovine serum albumin (BSA)-rabbit anti-BSA antibody complex, containing 2 mg antibody-nitrogen, was injected into bilateral rabbit knee-joints (10 animals per group) once a day for 6 days to induce allergic arthritis. The acid protease was administered intraarticularly once a day from the first day of the administration of the BSA-anti-BSA antibody complex. Ten days after the first administration of the complex, the rabbits were sacrificed. The knee-joints were fixed with formalin, stained with hematoxylin-eosin and microscopically examined. As a control, inactivated acid protease was given. The results are shown in Table 8.

In the control group, hyperplasia of synovial lining cells, pannus formation and cell infiltration of lymphoid follicles which are devoid of germinal centers were observed. In contrast, in the treated group, pannus formation and cell infiltration of lymphoid follicles were significantly decreased.

TABLE 8

| | Pathohistological observation | | |
|---|---|---|---|
| | Hyperplasia of synovial lining cells | Pannus formation | Cell infiltration of lymphoid follicles |
| Control | 10/10 | 9/10 | 8/10 |
| Acid protease | | | |
| 1 mg/kg | 10/10 | 5/10 | 4/10 |
| 3 mg/kg | 10/10 | 4/10* | 2/10* |
| 10 mg/kg | 10/10 | 3/10** | 2/10* |

Expressed as number of positive animals/number of animals used
*p < 0.05
**p < 0.01

EXPERIMENT 11

Hydrolysis of Human Immune Complex

Sera were collected from patients with rheumatoid arthritis, systemic lupus erythematosus (SLE) and hepatitis carrying immune complex. One ml portions of the sera were incubated with 10, 30 and 100 μg of the acid protease at 37° C. for 60 minutes. Then the immune complex content was determined by the hemolytic reaction of sheep red blood cells using guinea pig complement and taking human aggregated IgG as the standard, according to the method of Fust et al. (Atherosclerosis, 29, 181, 1978). Additionally, the sera from the patients with rheumatoid arthritis were assayed for rheumatoid factor (RA factor) by the hemagglutination reaction (RAHA test) by the method of Azuma et al. (The Ryumachi, 12, 330, 1972). The results are shown in Tables 9 and 10.

The acid protease decreased the immune complex content in the serum of these patients in a dose dependent manner. The acid protease also decreased the RA factor content of the patients with rheumatoid arthritis.

TABLE 9

| Hydrolysis of human immune complex | | | |
|---|---|---|---|
| Disease | Serum No. | Amount of acid protease added (μg/ml) | Immune complex content (μg/ml) |
| Rheumatoid arthritis | 1 | 0 | 75 |
| | | 10 | 63 |
| | | 30 | 52 |
| | | 100 | <50 |
| | 2 | 0 | 234 |
| | | 10 | 180 |
| | | 30 | 151 |
| | | 100 | 120 |
| | 3 | 0 | 103 |
| | | 10 | 84 |
| | | 30 | 63 |
| | | 100 | <50 |
| Systemic lupus erythematosus | 1 | 0 | 426 |
| | | 10 | 384 |
| | | 30 | 203 |
| | | 100 | 150 |
| | 2 | 0 | 120 |
| | | 10 | 74 |
| | | 30 | 56 |
| | | 100 | <50 |
| | 3 | 0 | 153 |
| | | 10 | 108 |
| | | 30 | 63 |
| | | 100 | 50 |
| Hepatitis | 1 | 0 | 63 |
| | | 10 | 59 |
| | | 30 | <50 |
| | | 100 | <50 |
| | 2 | 0 | 72 |
| | | 10 | 68 |
| | | 30 | 59 |
| | | 100 | 52 |

TABLE 10

| Effect on RA factor | | |
|---|---|---|
| Serum No. | Amount of acid protease added (μg/ml) | Maximum dilution to show positive reaction by RAHA |
| 1 | 0 | 2048 |
| | 10 | 1024 |
| | 30 | 256 |
| | 100 | 32 |
| 2 | 0 | 512 |
| | 10 | 128 |
| | 30 | 64 |
| | 100 | 64 |
| 3 | 0 | 1024 |
| | 10 | 512 |
| | 30 | 128 |
| | 100 | 64 |
| 4 | 0 | 256 |
| | 10 | 128 |
| | 30 | 64 |
| | 100 | 16 |

EXPERIMENT 12

Effect on the Growth of Cultured Human Breast Cancer Cells MX-1 and Mouse Leukemia Cells L1210

Human breast cancer cells MX-1 and mouse leukemia cells L1210 were respectively suspended at a cell concentration of $10^5$/ml in Eagle's medium containing 10% calf serum and test substances. The cells were cultured at 37° C. under 5% $CO_2$ for 48 hours. Then the number of viable cells was counted after staining with Tripan Blue. The growth inhibition rate was calculated according to the following equation and the results are shown in Table 11.

$$\text{Growth inhibition rate} = \left(1 - \frac{\text{Number of viable cells in treated group}}{\text{Number of viable cells in control}}\right) \times 100$$

TABLE 11

| | Concentration added (µg/ml) | Growth inhibition rate (%) | |
|---|---|---|---|
| | | MX-1 | L1210 |
| Acid protease | 30 | 15 | 8 |
| | 100 | 33 | 21 |
| | 300 | 55 | 30 |
| Mitomycin C | 100 | 47 | 62 |

The acid protease inhibited the growth of tumor cells even at a low concentration.

EXPERIMENT 13

Effect on Human Breast Cancer Cell MX-1 Bearing Nude Mice

A 2 mm-square piece of human breast cancer MX-1 was transplanted subcutaneously to a group of 5 nude mice (BALB/C, nu/nu). Two weeks after the transplantation, the acid protease was intravenously injected twice a day for 18 days. The tumor was weighed 32 days after the transplantation of the tumor. The results are shown in Table 12.

TABLE 12

| | Dose (mg/kg) | Weight of tumor (g) |
|---|---|---|
| Control | | 1.32 ± 0.09 |
| Acid protease | 0.3 | 0.79 ± 0.2* |
| | 3.0 | 0.65 ± 0.15* |

*$p < 0.05$

The acid protease exhibited significant antitumor effect.

EXPERIMENT 14

Effect on Leukemia Cells P388 Bearing Mice $10^5$ of leukemia cells P388 were transplanted intraperitoneally to a group of 5 BDF$_1$ male mice.

The acid protease was injected intravenously into the mice twice a day beginning on the next day until the animals died. The average life span was caluculated and expressed as a percentage of control. The results are shown in Table 13.

Average life span (%) = 
$$\frac{\text{Mean survival days of treated group}}{\text{Mean survival days of control group}} \times 100$$

TABLE 13

| | Dose (mg/kg) | Average life span (%) |
|---|---|---|
| Control | | 100 ± 5 |
| Acid protease | 0.3 | 110 ± 5 |
| | 1.0 | 121 ± 9 |
| | 3.0 | 123 ± 9* |
| Mitomycin C | 0.5 | 136 ± 17 |

*$p < 0.05$

The acid protease clearly increased average life span.

EXPERIMENT 15

Acute Toxicity

The acid protease dissolved in physiological saline was administered intravenously or intraperitoneally to a group of 10 ddY male mice weighing 20±1 g at a dose of 2 g/kg. The mice were kept under daily observation for any toxicological symptoms for a week. No sign of any toxicity was observed throughout the period.

As has been described in the above experiments, the acid protease which is the active ingredient of the pharmaceutical agent of the present invention suppressed production of IgE antibody and clearly exhibited a therapeutic effect on bronchial asthma. Furthermore, it clearly suppressed establishment and development of a number of diseases which are believed to be induced by immune complexes, for example, thyroiditis and nephritis. Moreover, the acid protease exhibited a strong antitumor effect.

The amount of the acid protease required to obtain these effects is within a sufficiently safe range, according to the result of the acute toxicity study. Since the acid protease is a protein of human origin, the probability that it would induce serious adverse reactions, such as anaphylactic shock due to its antigenicity, is beleved to be extremely small. Therefore it is believed to constitute a highly useful therapeutic agent for allergic disorders such as bronchial asthma, urticaria, hay fever, contact dermatitis, food allergy, drug allergy, allergic rhinitis, hypersensitivity pneumonitis, various immune complex diseases such as systemic lupus erythematosus, glomerulonephritis with immune complex, periarteritis nodosa, rheumatoid arthritis, immune complex hepatitis, thyroiditis, serum sickness, myasthenia gravis, various tumors such as gastric cancer, lung cancer, liver cancer, colon cancer, breast cancer, prostatic cancer, uterine cancer, bladder cancer, leukemia, esophagal cancer, lymphomas.

Although the agent of the present invention is generally prepared in the form of a solution for intravenous, subcutaneous, intramuscular or intraarticular injection, it may be used in the form of oral agent, inhalant or rectal suppository. Although the daily dose of the acid protease for an adult is in the range of from 1 to 1000 mg, preferably from 50 to 500 mg, it may be suitably increased or decreased depending on the symptom and the manner of application.

Preparations for injection may include lyophilized preparations which are dissolved immediately before administration, as well as liquid preparations. Oral preparations may include capsules, tablets, granules, powders and liquid oral preparations. Inhalant may include a lyophilized preparation. For rectal administration, the form of suppository may be used conveniently.

The acid protease of this invention can be formulated into agents by any of the conventional methods using pharmaceutically acceptable carriers or excipients. Example of solid carriers and excipients usable advantageously herein include common excipients such as lactose, mannitol, corn starch and potato starch, binders such as crystalline cellulose, cellulose derivatives, arabic gum, corn starch and gelatin; disintegrators such as corn starch, potato starch and calcium carbohydroxymethylcellulose; and lubricants such as talc and magnesium stearate. Examples of liquid carriers usable advantageously herein include distilled water for injection, physiological saline solution, vegetable oils for injection and glycols such as propylene glycol and polyethylene glycol.

Now, typical but non-limiting fomulations of the agent of this invention will be shown below.

FORMULATION 1

In 10 ml of physiological saline solution, 100 mg of the acid protease was dissolved. This solution was sterilized by filtering through a membrane filter. One ml of the filtrate was placed in a glass container sterilized in advance and then lyophilized. The container was then sealed to obtain lyophilized powder preparations.

FORMULATION 2

One hundred g of lyophilized acid protease, 97 g of lactose and 3 g of magnesium stearate were weighed and mixed to achieve homogeneity. Two hundred mg each of the resultant mixture was placed into No. 2 gelatin capsules and the capsules were coated with an enteric coating to give enteric capsules.

What is claimed is:

1. A method for treating patients suffering from allergic disorders or immune complex diseases, comprising administering an allergic disorder or immune complex disease treating effective amount of a human urinary acid protease to a patient suffering from such a disorder.

2. Method according to claim 1, wherein the acid protease has the following properties:
   (a) a molecular weight within the range 32,000 to 38,000 when determined by gel chromatography on Sephadex C-100,
   (b) an isoelectric point in the range of pH 1 to pH 3 determined by isoelectric focusing on Ampholine ®,
   (c) a maximum absorption at 278 nm,
   (d) excellent hydrolytic activity in an acidic range, pH value less than 7, when hemoglobin is used as a substrate,
   (e) positive reactivity to ninhydrin,
   (f) solubility in water and insolubility in ether and in chloroform,
   (g) inhibition by pepstatin, and
   (h) stability in acidic range, pH value less than 7, and instability in alkaline range, pH value over 8.

3. Method according to claim 1, wherein the daily administration dose of the acid protease is in a range of 1-1000 mg.

4. Method according to claim 3, wherein the daily administration dose is in a range of 50-500 mg.

5. Method according to claim 1, wherein the indication for the agent is allergic disorders.

6. Method according to claim 1, wherein the indication for the agent is immune complex diseases.

7. Method according to claim 1 or 2, wherein the agent is used in the form of a solution for injection.

8. Method according to claim 1 or 2, wherein the agent is used in the form of an oral preparation.

9. Method according to claim 1 or 2, wherein the agent is used in the form of a rectal suppository.

10. Method according to claim 1 or 2, wherein the agent is used in the form of an inhalant preparation.

11. Method according to claim 3, wherein the indication for the agent is allergic disorders.

12. Method according to claim 4, wherein the indication for the agent is allergic disorders.

13. Method according to claim 3, wherein the indication for the agent is immune complex diseases.

14. Method according to claim 4, wherein the indication for the agent is immune complex diseases.

15. Method according to claim 3, wherein the agent is used in the form of a solution for injection.

16. Method according to claim 4, wherein the agent is used in the form of a solution for injection.

17. Method according to claim 3, wherein the agent is used in the form of an oral preparation.

18. Method according to claim 4, wherein the agent is used in the form of an oral preparation.

19. Method according to claim 3, wherein the agent is used in the form of a rectal suppository.

20. Method according to claim 4, wherein the agent is used in the form of a rectal suppository.

21. Method according to claim 3, wherein the agent is used in the form of an inhalant preparation.

22. Method according to claim 4, wherein the agent is used in the form of an inhalant preparation.

* * * * *